(12) United States Patent
Roos et al.

(10) Patent No.: US 11,401,224 B2
(45) Date of Patent: Aug. 2, 2022

(54) METHOD FOR THE PREPARATION OF $C_3$—$C_{12}$-ALCOHOLS BY CATALYTIC HYDROGENATION OF THE CORRESPONDING ALDEHYDES

(71) Applicant: EVONIK OPERATIONS GMBH, Essen (DE)

(72) Inventors: Meike Roos, Büdingen (DE); René Poss, Karlsruhe (DE); Monika Berweiler, Maintal (DE); Markus Göttlinger, Rodenbach (DE); Stefan Wieland, Hanau (DE); Robert Franke, Marl (DE); Lena Altmann, Dorsten (DE)

(73) Assignee: Evonik Operations GmbH, Essen (DE)

( * ) Notice: Subject to any disclaimer, the term of this patent is extended or adjusted under 35 U.S.C. 154(b) by 38 days.

(21) Appl. No.: 16/969,607

(22) PCT Filed: Feb. 11, 2019

(86) PCT No.: PCT/EP2019/053236
§ 371 (c)(1),
(2) Date: Aug. 13, 2020

(87) PCT Pub. No.: WO2019/158456
PCT Pub. Date: Aug. 22, 2019

(65) Prior Publication Data
US 2021/0032185 A1 Feb. 4, 2021

(30) Foreign Application Priority Data

Feb. 14, 2018 (EP) .................................. 18156599

(51) Int. Cl.
*C07C 29/141* (2006.01)
*B01J 25/02* (2006.01)
*B01J 35/10* (2006.01)

(52) U.S. Cl.
CPC ............. *C07C 29/141* (2013.01); *B01J 25/02* (2013.01); *B01J 35/1009* (2013.01); *B01J 35/1014* (2013.01); *B01J 35/1019* (2013.01); *B01J 35/1076* (2013.01)

(58) Field of Classification Search
CPC ...... C07C 29/141; C07C 31/125; B01J 25/02; B01J 35/1009; B01J 35/1014; B01J 35/1019; B01J 35/1076
See application file for complete search history.

(56) References Cited

U.S. PATENT DOCUMENTS

| | | |
|---|---|---|
| 1,628,190 A | 5/1927 | Raney |
| 1,915,473 A | 6/1933 | Raney |
| 2,139,602 A | 12/1938 | Raney |
| 2,895,819 A | 7/1959 | Fiedler |
| 2,967,893 A | 1/1961 | Hort et al. |
| 2,977,327 A | 3/1961 | Raney |
| 4,049,580 A | 9/1977 | Oden et al. |
| 5,399,793 A | 3/1995 | Vargas et al. |
| 6,262,317 B1 | 7/2001 | Becker et al. |
| 6,399,793 B1 | 6/2002 | Kronenthal et al. |
| 6,969,780 B1 | 11/2005 | Dubner et al. |
| 7,524,996 B2 | 4/2009 | Lorenz et al. |
| 7,538,254 B2 | 5/2009 | Lorenz et al. |
| 7,572,941 B2 | 8/2009 | Lorenz et al. |
| 7,605,292 B2 | 10/2009 | Lorenz et al. |
| 7,612,241 B2 | 11/2009 | White et al. |
| 9,029,290 B2 | 5/2015 | Lee et al. |
| 9,346,079 B2 | 5/2016 | Lee et al. |
| 9,567,276 B2 | 2/2017 | Klasovsky et al. |
| 9,598,537 B2 | 3/2017 | Roos et al. |
| 9,943,818 B2 | 4/2018 | Jin et al. |
| 11,090,637 B2 | 8/2021 | Wieland et al. |
| 2002/0151751 A1 | 10/2002 | Ostgard et al. |
| 2002/0193618 A1 | 12/2002 | Ostgard et al. |
| 2003/0047505 A1 | 3/2003 | Grimes et al. |
| 2004/0199019 A1 | 10/2004 | Schmidt |
| 2011/0011772 A1 | 1/2011 | Schmidt |
| 2012/0154983 A1 | 6/2012 | Zhang et al. |
| 2014/0038816 A1 | 2/2014 | Bakker et al. |
| 2014/0221700 A1 | 8/2014 | Radivojevic et al. |
| 2018/0230081 A1 | 8/2018 | Rüfer et al. |
| 2019/0210010 A1 | 7/2019 | Pinkos et al. |

(Continued)

FOREIGN PATENT DOCUMENTS

| CA | 2 823 676 | 8/2012 |
|---|---|---|
| DE | 102 45 510 | 4/2004 |

(Continued)

OTHER PUBLICATIONS

International Search Report for PCT/EP2020/076823 (international counterpart of copending U.S. Appl. No. 17/059,448), filed Sep. 25, 2020.
Written Opinion of the International Searching Authority for PCT/EP2020/076823 (international counterpart of copending U.S. Appl. No. 17/059,448), filed Sep. 25, 2020.
Non Final Office for copending U.S. Appl. No. 16/338,015, dated Mar. 5, 2021.
U.S. Appl. No. 17/053,340, filed Nov. 5, 2020, Poss.
U.S. Appl. No. 17/059,448, filed Nov. 29, 2020, Roos.
International Preliminary Report on Patentability for PCT/EP2019/053236 (international counterpart of corresponding U.S. Appl. No. 16/969,607), filed Feb. 11, 2019.

(Continued)

*Primary Examiner* — Jafar F Parsa
(74) *Attorney, Agent, or Firm* — Law Office of: Michael A. Sanzo, LLC

(57) ABSTRACT

The present invention relates to a process for preparing $C_3$-$C_{12}$ alcohols by catalytically hydrogenating the corresponding aldehydes at a temperature in the range of 50-250° C. and a pressure in the range of 5-150 bar in the presence of a supported activated Raney-type catalyst, characterized in that the support body is a metal foam and the metal is selected from the group consisting of cobalt, nickel and copper and mixtures thereof.

20 Claims, 3 Drawing Sheets

(56) References Cited

U.S. PATENT DOCUMENTS

| | | | |
|---|---|---|---|
| 2019/0232256 | A1 | 8/2019 | Berweiler et al. |
| 2019/0232257 | A1 | 8/2019 | Weiland et al. |
| 2019/0344248 | A1 | 11/2019 | Pinkos et al. |
| 2020/0016579 | A1 | 1/2020 | Schreiber et al. |
| 2020/0016583 | A1 | 1/2020 | Merkel et al. |
| 2021/0275996 | A1 | 9/2021 | Roos et al. |
| 2021/0276091 | A1 | 9/2021 | Poss et al. |

FOREIGN PATENT DOCUMENTS

| | | |
|---|---|---|
| EP | 0 340 970 | 11/1989 |
| EP | 0 807 464 | 11/1997 |
| EP | 2 764 916 | 8/2014 |
| EP | 3 115 106 | 1/2017 |
| GB | 1 242 358 | 8/1971 |
| WO | WO 02/055453 | 7/2002 |
| WO | WO 2005/039764 | 5/2005 |
| WO | WO 2007/028411 | 3/2007 |
| WO | WO 2008/151614 | 12/2008 |
| WO | WO 2018/060245 | 4/2018 |
| WO | WO 2018/060269 | 4/2018 |
| WO | WO 2021/058702 | 4/2021 |
| WO | WO 2021/058703 | 4/2021 |
| WO | WO 2021/058704 | 4/2021 |
| WO | WO 2021/058705 | 4/2021 |
| WO | WO 2021/058706 | 4/2021 |
| WO | WO 2021/058719 | 4/2021 |

OTHER PUBLICATIONS

European Search Report and Search Opinion for EP 18 15 6599 (European counterpart of corresponding U.S. Appl. No. 16/969,607), filed Feb. 14, 2018, with English language machine translation of the Search Opinion attached.

English language machine translation of the European Search Opinion for EP 16 19 1735, (international counterpart of copending U.S. Appl. No. 16/338,015), filed Sep. 30, 2016.

English language machine translation of the European Search Opinion for EP 16 19 1751, (international counterpart of copending U.S. Appl. No. 16/338,044), filed Sep. 30, 2016.

Ullmann's Encyclopedia of Industrial Chemistry: G. Eigenberger, W. Ruppel: "Catalytic Fixed-Bed Reactors", Wiley-VCH, online ISBN: 9783527306732 | DOI: 10.1002/14356007; 2012).

Ullmann's Encyclopedia of Industrial Chemistry: D. Sanfilippo, P.N. Rylander: "Hydrogenation and Dehydrogenation", Wiley-VCH, online ISBN: 9783527306732 | DOI: 10.1002/14356007; 2012).

Response to Restriction Requirement for copending U.S. Appl. No. 16/338,015, filed Dec. 23, 2020.

International Search Report for corresponding PCT/EP2019/053236 filed Feb. 11, 2019.

Written Opinion of the International Searching Authority for corresponding PCT/EP2019/053236 filed Feb. 11, 2019.

International Search Report for PCT/EP2017/074528 (international counterpart of copending U.S. Appl. No. 16/338,015), filed Sep. 27, 2017.

Written Opinion of the International Searching Authority for PCT/EP2017/074528 (international counterpart of copending U.S. Appl. No. 16/338,015), filed Sep. 27, 2017.

International Preliminary Report on Patentability for PCT/EP2017/074528 (international counterpart of copending U.S. Appl. No. 16/338,015), filed Sep. 27, 2017.

European Search Report and Search Opinion for EP 16 19 1735 (European counterpart of copending U.S. Appl. No. 16/338,015), filed Sep. 30, 2016.

International Search Report for PCT/EP2017/074491 (international counterpart of copending U.S. Appl. No. 16/338,044), filed Sep. 27, 2017.

Written Opinion of the International Searching Authority for PCT/EP2017/074491 (international counterpart of copending U.S. Appl. No. 16/338,044), filed Sep. 27, 2017.

International Preliminary Report on Patentability for PCT/EP2017/074491 (international counterpart of copending U.S. Appl. No. 16/338,044), filed Sep. 27, 2017.

European Search Report and Search Opinion for EP 16 19 1751 international counterpart of copending U.S. Appl. No. 16/338,044), filed Sep. 30, 2016.

Abdullah, et al., "The use of bulk density measurments as flowability indicators," Powder Technology 102(2):151-165 (May 1999).

Brunauer, et al., "Adsorption of Gases in Multimolecular Layers," J. Am. Chem. Soc. 60:309-319 (Feb. 1938).

Brunet Espinosa, "Ni in CNFs: Highly Active for Nitrate Hydrogenation," ACS Catalysis 6:5432-5440 (2016).

Coleman, et al., "Evaluation of Foam Nickel for the Catalytic Partial Oxidation of Methane," Catalysis Letters 128(1-2):144-153 (Nov. 2008).

Haibin, et al., "Polymer-supported catalysts for clean preparation of n-butanol," Catalysis Science & Technology 4(8):2499-2503 (May 2014).

Kolaczkowski, et al., "Potential for metal foams to act as structured catalysy supports in fixed-bed reactors," CatalysisToday 273:221-233 (2016).

Li, et al., "Ni-$Al_2O_3$/Ni-Foam Catalyst with Enhanced Heat Transfer for Hydrogenation of $CO_2$ to Methane," AIChE Journal 61(12):4323-4331 (Dec. 2015).

Liu, et al., :Monolithic catalysts with Pd deposited on a structured nickel foam packing, Catalysis Today 273:34-40 (Apr. 2016).

Luther, E. et al., "Nonostructured Metal Foams: Synthesis and Applications," PowderMet2009, Las Vegas, NV, Los Alamos National Laboratory, 12 pages (2009).

Petró, et al., "A new alumina-supported, not pyrophoric Raney-type Ni-catalyst," Applied Catalysis A: General 190:73-86.

Ullman's Encyclopedia of Industrial Chemistry, "Metal Foams" chapter, publisned online on Jul. 15, 2012, DOI: 25 10.1002/14356007.c16_c01.pub2.

Office Action dated Sep. 18, 2019 for copending U.S. Appl. No. 16/338,044.

Response to Office Action filed Jan. 8, 2020 for copending U.S. Appl. No. 16/338,044.

Office Action dated Mar. 9, 2020 for copending U.S. Appl. No. 16/338,044.

Response to Office Action for copending U.S. Appl. No. 16/338,044, filed Aug. 9, 2020.

U.S. Appl. No. 16/338,015, filed Mar. 29, 2019, US-2019/0232256 A1, Aug. 1, 2019, Berweiler.

U.S. Appl. No. 16/338,044, filed Mar. 29, 2019, US-2019/0232257 A1, Aug. 1, 2019, Weiland.

Restriction Requirement dated Oct. 26, 2020, for copending U.S. Appl. No. 16/338,015.

Notice of Allowance dated Sep. 28, 2020, for copending U.S. Appl. No. 16/338,044.

Amendment & Response for copending U.S. Appl. No. 16/338,015, filed Jun. 30, 2021.

Ex Parte Quale Action for copending U.S. Appl. No. 16/338,015, dated Aug. 10, 2021.

Response to Ex Parte Quale Action for copending U.S. Appl. No. 16/338,015, filed Oct. 10, 2021.

Notice of Allowance for copending U.S. Appl. No. 16/338,015, dated Oct. 25, 2021.

METHOD FOR THE PREPARATION OF $C_3$—$C_{12}$-ALCOHOLS BY CATALYTIC HYDROGENATION OF THE CORRESPONDING ALDEHYDES

CROSS REFERENCE TO RELATED APPLICATIONS

The present application is US national stage of international application PCT/EP2019/053236, which had an international filing date of Feb. 11, 2019, and which was published on Aug. 22, 2019. Priority is claimed to European application 18156599.5, filed on Feb. 14, 2018. The contents of these prior applications is hereby incorporated by reference in their entirety.

FIELD OF THE INVENTION

The present invention relates to a process for preparing $C_3$-$C_{12}$ alcohols by catalytically hydrogenating the corresponding aldehydes at a temperature in the range of 50-250° C. and a pressure in the range of 5-150 bar in the presence of a supported activated Raney-type catalyst, characterized in that the support body is a metal foam and the metal is selected from the group consisting of copper, nickel and cobalt and mixtures thereof.

BACKGROUND OF THE INVENTION

The essential field of work in the mineral oil-processing industry is the processing of unsaturated hydrocarbons from mineral oil refining to give raw materials for the chemicals industry. Aldehydes are obtained from the oxo process, and are then processed further under heterogeneous catalysis to give alcohols. According to the carbon chain length, the resulting alcohols are used in a wide variety of different applications, for example as plasticizers for plastics or as raw materials for specific syntheses. Hydrogenations of oxo process aldehydes are nowadays effected on the industrial scale typically in heterogeneously catalysed continuous processes over oxidically supported mixed metal catalysts (U.S. Pat. No. 5,399,793), which are used in the form of shaped bodies in beds. Typically, the temperatures are within a range of 120-200° C. and the pressures within a range of 25-350 bar. As a result of the continuous circulation mode, the input concentration of aldehydes is crucially diluted by the product; thus, the formation of local hotspots as a result of the exothermicity of the reaction is firstly reduced and, secondly, the chemical equilibrium of the side reactions is moved. The service life of these catalysts is limited. As well as thermal ageing processes, for example, the deposition of unwanted by-products (fouling) leads to deactivation of the catalysts. Studies on this process can be found in the thesis by Arne Reinsdorf ("Deaktivierung heterogener Katalysatoren zu Hydrierung von Oxo-Alkoholen" [Deactivation of Heterogeneous Catalysts for Hydrogenation of Oxo Process Alcohols]; Thesis 2017, University of Bayreuth, Arne Reinsdorf, Shaker Verlag). In addition, the customary catalysts show a not inconsiderable proportion of unwanted abrasion.

Supported activated Raney-type catalysts per se are known to those skilled in the art, for example from U.S. Pat. No. 4,049,580, Applied Catalysis A: General 190 (2000) 73-86, or WO2007/028411. Typically, this is understood to mean metal alloys that have been applied to metallic or oxidic or carbonaceous supports and have been activated by leaching. Just like the pulverulent Raney-type catalysts, catalysts of this kind are suitable for numerous reactions, for example isomerizations, hydrogenations, reductive aminations, reductive alkylations, dehydrogenations, or hydrogenolyses. By virtue of their size and shape, however, they enable a continuous reaction regime, which is possible with powder catalysts only with a high level of apparatus complexity. Therefore, the supported activated Raney-type catalysts are also counted among the fixed bed catalysts.

The term "metal foams" is well-established in the technical literature; see also Ullmann's Encyclopedia of Industrial Chemistry, "Metallic Foams" chapter, published online on 15 Jul. 2012, DOI: 25 10.1002/14356007.c16_c01.pub2. "Metal foams" are understood to mean rigid metallic foams having a high porosity and numerous interconnections between regions of solid material with irregular structure. Such metal foams are also known as "cellular metals", but the term "metal foams" is more commonly used. Nickel foams find use, for example, as electrodes in batteries or as filtration elements.

Catalytic applications of materials based on metal foams are very limited. Metal foam bodies have usually been used to date for heterogeneously catalysed gas phase reactions. These applications especially include catalytic aftertreatment of exhaust gases from internal combustion engines, catalytic purification of flue gases, the water-gas shift reaction for preparation of hydrogen from carbon monoxide and water vapour, or steam reforming of methane. In such applications, the backpressure built up by the metal foam bodies in the flowing reaction medium is comparatively low owing to their high porosity.

SUMMARY OF THE INVENTION

There is a need for a process for hydrogenation of aldehydes, especially aldehydes from the oxo process, which features good activity and selectivity and simultaneously leads to an improved service life of the catalyst by virtue of a lower tendency to fouling and improved abrasion resistance.

This object is achieved by a process for preparing $C_3$-$C_{12}$ alcohols by catalytically hydrogenating the corresponding aldehydes at a temperature in the range of 50-250° C. and a pressure in the range of 5-150 bar in the presence of a supported activated Raney-type catalyst, characterized in that the support body is a metal foam and the metal is selected from the group consisting of cobalt, nickel and copper and mixtures thereof.

BRIEF DESCRIPTION OF THE DRAWINGS

FIG. 1A is a schematic drawing showing a process by which surface-modified foam bodies can be made.

FIG. 1B shows shaped metal foam bodies.

FIG. 2 shows a circulation reactor used in Examples 1 and 2.

DETAILED DESCRIPTION OF THE INVENTION

The supported activated Raney-type catalysts used in the process according to the invention are known, for example, from EP2764916A1. They are referred to therein as surface-modified metal foam bodies. One process by which they can be obtained is that described hereinafter (cf. FIG. 1A):

(1) A commercially available metal foam is treated with an adhesion promoter and then coated with aluminium powder. Suitable adhesion promoters are, for example, polyvinylpyrrolidone or polyethyleneimine solution. What is called a supported aluminium powder is obtained.

(2) In a subsequent heat treatment with exclusion of oxygen, aluminium in metal foam is dissolved to form intermetallic phases and the adhesion promoter is simultaneously removed. Structure and pore structure of the metal foam are fully conserved here. The heat treatment is preferably conducted within a temperature range of 500-1000° C. What is called a supported alloy is obtained, which is not catalytically active.

Figure 1:
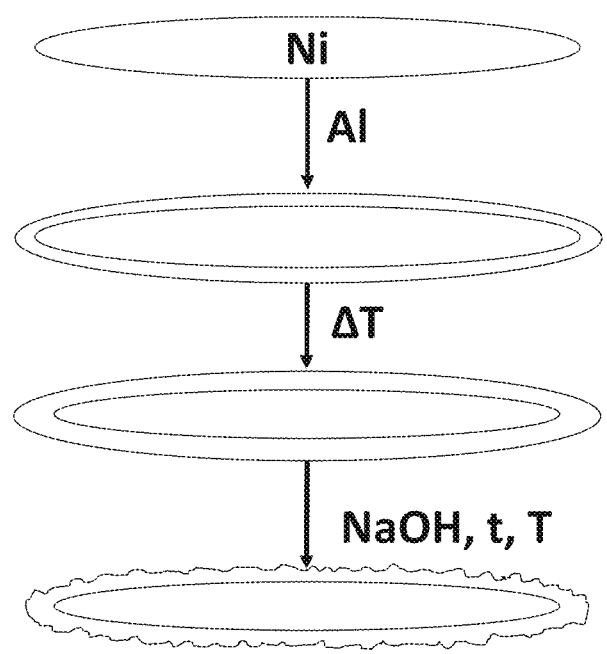
FIG. 1A.
FIG. 1B.
Figure 1:
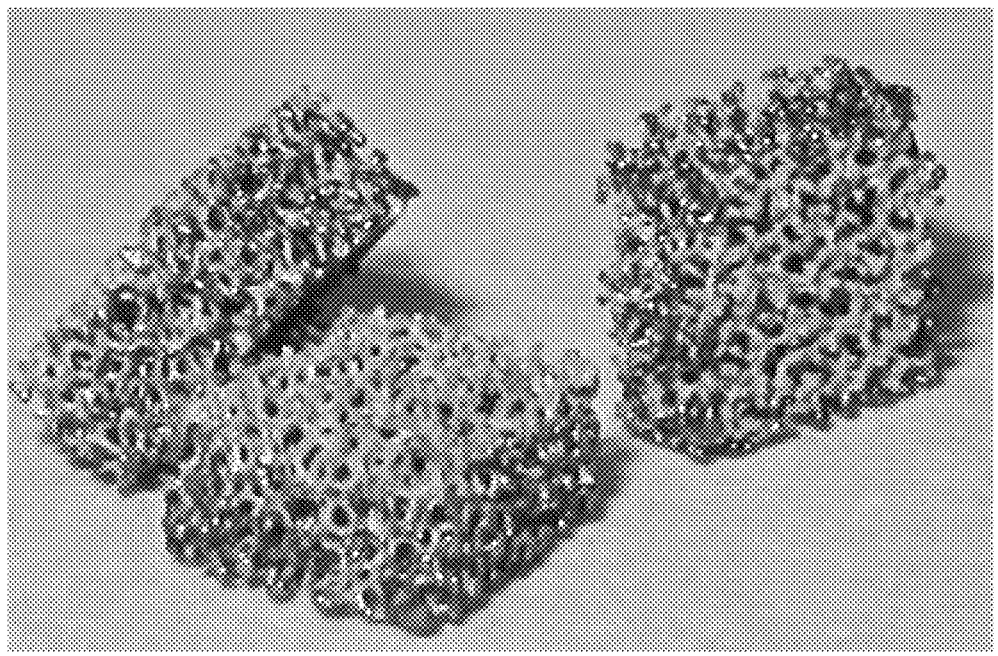

(3) The heat treatment may be followed by a comminution and/or individualization of the material, for example by laser cutting or by laser jet cutting, if this has not already been done in a shaping step prior to the heat treatment (cf. FIG. 1 B).

(4) Subsequently, supported activated Raney-type catalysts are produced by removing at least a portion of the aluminium present in the alloy by dissolution. This step is also referred to as leaching. Aqueous basic solutions are used for this purpose, preferably alkali metal hydroxide solutions, where the alkali metal hydroxide is selected from the group consisting of sodium hydroxide, potassium hydroxide or lithium hydroxide. Aqueous sodium hydroxide solution is particularly preferred. The concentration of the aqueous alkali metal hydroxide solution used in this process step is generally in a range between 0.1-60% by weight. The leaching of the aluminium is preferably effected with a 5-50% by weight, more preferably 5-35% by weight, aqueous sodium hydroxide solution at a temperature in the range of 20-100° C., preferably within a range of 40-85° C., more preferably within a range of 50-80° C. The leaching times to be employed, i.e. the reaction times of the sodium hydroxide solution with the aluminium-alloyed metal foam, may be between 2 and 300 minutes.

The support body of the supported activated Raney-type catalyst is a metal foam, and the metal is selected from the group consisting of cobalt, nickel and copper and mixtures thereof. The metal is preferably nickel.

The supported activated Raney-type catalysts used in accordance with the invention do not contain any organic components, i.e. the sum of the proportions by weight of carbon and carbon-containing compounds is less than 0.1% by weight of the total weight of the catalyst.

The hydrogenation is generally conducted at a pressure of 5-150 bar and at a temperature of generally 50-250° C. Preferably, hydrogenation is conducted at a pressure in the range of 10-100 bar and a temperature in the range of 80-200° C.; more preferably, the hydrogenation is conducted at a pressure in the range of 15-50 bar and a temperature in the range of 100-200° C. Most preferably, the hydrogenation is conducted at a pressure of 20-30 bar and at a temperature in the range of 100-160° C.

Optionally, the hydrogenation can be performed in the presence of a solvent that is inert under the hydrogenation conditions, for example hydrocarbons or alcohols, and the solvent used may more preferably be the alcohol corresponding to the aldehyde hydrogenation product.

Hydrogenation can be accomplished using pure hydrogen, but it is also possible to use hydrogen mixtures in admixture with gases that are inert under the reaction conditions.

With regard to the aldehyde, there are no restrictions in the process according to the invention; it is possible to hydrogenate either aliphatic or aromatic $C_3$-$C_{12}$ aldehydes to the corresponding alcohols. If aliphatic aldehydes containing C—C double bonds are used, the hydrogenation generally gives rise to the corresponding saturated alcohol. Merely owing to the industrial significance of the alcohols used, the process is limited to the preparation of $C_3$-$C_{12}$ alcohols by the catalytic hydrogenation of the corresponding $C_3$-$C_{12}$ aldehydes, although the process according to the invention is also of good suitability for hydrogenation of other aldehydes to the corresponding alcohols. The process is of particularly good suitability for preparation of $C_3$ to $C_{12}$ alcohols, such as propanol, n-butanol, isobutanol, n-pentanol, isopentanol, 1-nonanol, isononanol, 2-ethylhexanol and 2-propylheptanol from the corresponding alkanal or alkenal precursors, which have preferably been obtained by hydroformylation of olefins or olefin mixtures and optionally the subsequent alcohol condensation thereof. In the process according to the invention, preference is given to using a $C_3$-$C_9$ aldehyde, particular preference to using isononanal or butyraldehyde as aldehyde. More preferably, the aldehyde is an aldehyde from an oxo process.

In a particular embodiment of the invention, the supported activated Raney-type catalyst contains 85-95% by weight of nickel and 5-15% by weight of aluminium, based on the total weight of the catalyst. In a preferred embodiment, the supported activated Raney-type catalyst additionally contains up to 3% by weight of molybdenum, based on the total weight of the catalyst; the molybdenum content is more preferably 0.2-1.5% by weight.

In a further particular embodiment, the supported activated Raney-type catalyst has the following properties:
a. BET surface area: 1-200 m²/g, preferably 5-100 m²/g, more preferably 5-50 m²/g; and
b. macroscopic pores in the range of 100-5000 µm.

In a further particular embodiment of the invention, the supported activated Raney-type catalyst is cylindrical, annular, cuboidal, parallelepipedal or cubic. In a further configuration of this embodiment, the supported activated Raney-type catalyst is used in the form of a fixed bed of bulk material. In the form of a cuboidal catalyst, it preferably has a maximum edge length of 50 mm; it more preferably has a maximum edge length of 2-20 mm.

The hydrogenation of the aldehydes can generally be performed continuously or batchwise, preference being given to continuous performance.

The supported activated Raney-type catalyst is preferably arranged in fixed beds in reactors operated in liquid phase mode or trickle mode. For continuous hydrogenation, it is possible to use tubular reactors or reactor cascades, for example, and loop reactors, optionally with recycling of partly hydrogenated aldehyde streams, have been found particularly advantageous.

EXAMPLES

Abbreviations:

$$INAL = \text{isononanal}$$

$$INA = \text{isononanol}$$

$$WHSV = \text{Weight Hourly Space Velocity} \left( \frac{\dot{m}_{reactant}}{m_{cat}} \right)$$

$$LHSV = \text{Liquid Hourly Space Velocity} \left( \frac{\dot{V}_{liquid}}{V_{cat}} \right)$$

$$X(INAL) = \text{conversion of isononanal}$$

$$S(INA) = \text{selectivity for isononanol}$$

Preparation of Catalysts:

Catalyst 1 (Supported Activated Nickel Foam)

A nickel foam commercially available as roll material and having a thickness of 1.9 mm, a width of 300 mm and an average pore size of 580 μm was sprayed with a commercially available polyethyleneimine adhesion promoter solution, coated with likewise commercially available aluminium powder having a particle size <63 μm ($d_{50}$≈40 μm), and subjected to a heat treatment with exclusion of oxygen at 725° C. The mass ratios of nickel foam used and aluminium powder were chosen here such that the ratio of aluminium to the total mass of the supported alloy was 28±2%. After cooling, the material was comminuted with a laser into cuboidal particles having an edge length of 4×4×1.9 mm. The resulting bulk material was activated by treatment in a 10% by weight sodium hydroxide solution at 60° C. for 60 minutes. Subsequently, the catalyst was washed with demineralized water until a pH of <10 had been attained.

Catalyst 2 (Molybdenum-Doped)

2.24 g of $MoO_3$ were dissolved in 100 ml of boiling demineralized water by gradual addition of 1.48 g of $Na_2CO_3$. Once the $MoO_3$ had dissolved, the solution was made up to 150 ml.

160 g of supported activated nickel foam in water were washed with ammonium chloride solution until a pH of the supernatant solution of 7.5-8 had been attained. Then the catalyst was impregnated with the molybdate solution at 40° C. until no molybdenum was detectable any longer in the solution with Merckoquant or Quantofix test strips. Subsequently, the catalyst was washed twice with demineralized water.

The composition of catalysts 1 and 2 was analysed by ICP-OES; the results are reported in Table 1 below.

TABLE 1

|  | Catalyst 1 | Catalyst 2 |
| --- | --- | --- |
| Nickel (% by wt.) | 88 | 87 |
| Aluminium (% by wt.) | 11 | 11.3 |
| Molybdenum (% by wt.) | — | 0.74 |
| Bulk material (mm) | 4*4*1.9 | 4*4*1.9 |

Use Example 1 (Inventive)—Hydrogenation of Isononanal Over Catalyst 1 or Catalyst 2

Figure 2:
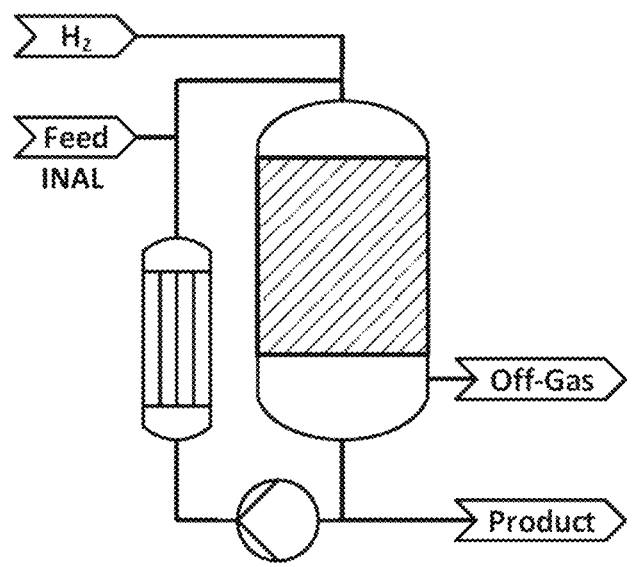
FIG. 2.

In a first experiment, catalyst 1 was positioned in a circulation reactor (cf. FIG. 2) in the form of a fixed bed of bulk material. At a constant hydrogen pressure of 25 bar, the reactor was supplied continuously with isononanal, with a simultaneous circulation flow rate of 25 l/h through the fixed bed and establishment of an $H_2$ offgas rate of 5 l/h. Further reaction parameters can be found in Table 2. The reaction conditions were chosen such that, in the continuous operation established, isononanal conversion rates of 97.5% were achieved.

The experiment was repeated with catalyst 2.

Use Example 2 (Comparative Experiment)—Hydrogenation of Isononanal Over Specialyst 103

The experiment described in Use example 1 was repeated with the comparative catalyst Specialyst 103 from Evonik Industries (catalyst 3). The detailed experimental conditions can be found in Table 2. The preparation, composition and structure of Specialyst 103 are disclosed in EP 3 037 400 B1 (cf. in particular paragraphs 0024 and 0027 therein).

TABLE 2

|  | Catalyst 1 | | Catalyst 2 | | Catalyst 3 | |
| --- | --- | --- | --- | --- | --- | --- |
| Pressure [bar] | 25 | | | | | |
| Circulation flow rate [l/h] | 25 | | | | | |
| $H_2$ offgas [l/h] | 5 | | | | | |
| Temperature [° C.] | 150 | 170 | 150 | 170 | 150 | 180 |
| INAL feed (l/h) | 0.76 | 1.5 | 0.76 | 1.5 | 0.76 | 0.76 |
| WHSV [$h^{-1}$] | 8 | 15 | 8 | 15 | 4 | 5.5 |
| LHSV [$h^{-1}$] | 4 | 8 | 4 | 8 | 3.5 | 4 |
| X (INAL) | 98 | 98.5 | 98.5 | 98.6 | 94 | 97.6 |
| S (INA) | 102 | 102 | 102.6 | 102 | — | ~102 |

Since the experiments were run at the same conversion (X(INAL)≥97.5%), the following can be inferred from the results:

With catalyst 3 (comparative experiment), the target conversion is achieved under the reaction conditions chosen with a temperature of 180° C.

At a load of 760 ml/h, both catalyst 1 and catalyst 2 already reach this target conversion at a temperature of 150° C.

At a load of 1500 ml/h, both catalyst 1 and catalyst 2 already reach this target conversion at a temperature of 170° C.

The supported activated Raney-type catalysts have a much higher activity than the comparative catalyst based on the catalyst volume. These catalysts reach identical conversions to the catalyst according to prior art even when the amount of the INAL reactant metered in is doubled. Given the same reactor size, doubling of the production volume per unit time is thus possible.

The crucial advantage of the supported activated Raney-type catalysts over the comparative catalyst is the fact that comparable conversions and yields can be achieved at much lower temperature. It is known from the thesis by Arne Reinsdorf ("Deaktivierung heterogener Katalysatoren zu Hydrierung von Oxo-Alkoholen"; Thesis 2017, University of Bayreuth, Arne Reinsdorf, Shaker Verlag) that the reaction temperature in particular has a great influence on the formation of high-boiling oligomers. These oligomers in turn are responsible for catalyst fouling and resultant limitations on service life. The use of supported activated Raney-type catalysts in the process according to the invention enables lowering of the reaction temperature without production losses. The lowering of the operating temperature results in a decline in aldol condensation reactions that can result in high-boiling oligomers. It is to be expected that a production plant which is operated by the process according to the invention will achieve higher production outputs with simultaneously elevated service life of the catalysts and hence will work in a more energy- and resource-efficient manner than production plants according to the prior art.

Use Example 3 (Inventive)—Hydrogenation of Butyraldehyde

In a stirred tank autoclave having a volume of 0.65 l, catalyst 1 (volume: 5 ml) is positioned in a catalyst basket having an internal volume of 7 ml directly above the stirrer unit at a distance of 5 mm from the reactor wall, such that the catalyst is arranged optimally in the sparging zone of the reactor. Before the start of the reaction, butyraldehyde is pumped into the reactor in water as solvent, heated to 100°

C. while stirring at 100 rpm and pressurized to 80 bar with hydrogen. The reaction was started by increasing the stirrer speed to 1000 rpm. The reaction was stopped once no significant absorption of hydrogen per unit time was observed any longer. The reaction mixture was cooled down to 40° C. and the reactor was emptied. Further reaction conditions and the conversion of butyraldehyde to 1-butanol achieved are reported in Table 3.

TABLE 3

|  | Catalyst 1 |
|---|---|
| Hydrogen pressure [bar] | 80 |
| Temperature [° C.] | 100 |
| LHSV [h$^{-1}$] | 2.6 |
| Conversion | 98.3 |

This experiment shows that the process according to the invention can also be used to hydrogenate other aldehydes, such as butyraldehyde here, with good results in conversion and yield.

The process according to the invention thus has the following advantages resulting from the use of supported activated Raney-type catalysts:

Broad field of use, suitable for all $C_3$-$C_{12}$ aldehydes
No activation with alkali in the reactor necessary
Allows lower reaction temperature (costs)
Reduces formation of thermal by-products
Mechanically stable (no abrasion in filling or operation)
Very low pressure drop

The invention claimed is:

1. A process for preparing $C_3$-$C_{12}$ alcohols by catalytically hydrogenating the corresponding aldehydes at a temperature in the range of 50-250° C. and a pressure in the range of 5-150 bar in the presence of a supported activated Raney-type catalyst, wherein the supported activated Raney-type catalyst comprises a support body that is a metal foam and the metal is selected from the group consisting of: cobalt; nickel; copper; and mixtures thereof.

2. The process of claim 1, wherein a $C_3$-$C_9$ aldehyde is used in the hydrogenation.

3. The process of claim 1, wherein isononanal or butyraldehyde is used as the aldehyde in the hydrogenation.

4. The process of claim 1, wherein the metal is nickel.

5. The process of claim 1, wherein the supported activated Raney-type catalyst contains 85-95% by weight of nickel and 5-15% by weight of aluminium, based on the total weight of the catalyst.

6. The process of claim 5, wherein the supported activated Raney-type catalyst additionally contains up to 3% by weight of molybdenum, based on the total weight of the catalyst.

7. The process of claim 1, wherein the supported activated Raney-type catalyst has the following properties:
a) a BET surface area of 1-200 m$^2$/g, and
b) macroscopic pores in the range of 100-5000 μm.

8. The process of claim 1, wherein the supported activated Raney-type catalyst is cylindrical, annular, cuboidal, parallelepipedal or cubic.

9. The process of claim 8, wherein the supported activated Raney-type catalyst is used in the form of a fixed bed of bulk material.

10. The process of claim 9, wherein the supported activated Raney-type catalyst is cuboidal and has a maximum edge length of 50 mm.

11. The process of claim 1, wherein the hydrogenation is conducted continuously.

12. The process of claim 1, wherein the aldehyde is obtained by an oxo process.

13. The process of claim 5, wherein the supported activated Raney-type catalyst has the following properties:
a) a BET surface area of 1-200 m$^2$/g, and
b) macroscopic pores in the range of 100-5000 μm.

14. The process of claim 13, wherein the supported activated Raney-type catalyst is cylindrical, annular, cuboidal, parallelepipedal or cubic.

15. The process of claim 14, wherein the supported activated Raney-type catalyst is used in the form of a fixed bed of bulk material.

16. The process of claim 15, wherein the supported activated Raney-type catalyst is cuboidal and has a maximum edge length of 50 mm.

17. The process of claim 13, wherein the hydrogenation is conducted continuously.

18. The process of claim 13, wherein the aldehyde is obtained by an oxo process.

19. The process of claim 13, wherein a $C_3$-$C_9$ aldehyde is used in the hydrogenation.

20. The process of claim 13, wherein isononanal or butyraldehyde is used as the aldehyde in the hydrogenation.

* * * * *